(12) United States Patent
Bonin (10) Patent No.: US 8,720,256 B2
(45) Date of Patent: May 13, 2014

(54) OFF-AXIS IMAGING FOR INDENTATION INSTRUMENTS

(76) Inventor: Wayne Allen Bonin, North Oaks, MN (US)

( * ) Notice: Subject to any disclaimer, the term of this patent is extended or adjusted under 35 U.S.C. 154(b) by 105 days.

(21) Appl. No.: 12/655,935

(22) Filed: Jan. 11, 2010

(65) Prior Publication Data

US 2010/0107745 A1    May 6, 2010

Related U.S. Application Data

(63) Continuation-in-part of application No. 11/708,302, filed on Feb. 20, 2007, now Pat. No. 7,647,822.

(51) Int. Cl.
*G01B 5/28* (2006.01)

(52) U.S. Cl.
USPC ............................................................. 73/105

(58) Field of Classification Search
USPC .......................................................... 73/105
See application file for complete search history.

(56) References Cited

U.S. PATENT DOCUMENTS

| 4,468,136 | A | * | 8/1984 | Murphy et al. | ................. | 374/45 |
| 5,714,756 | A | * | 2/1998 | Park et al. | ......................... | 850/6 |
| 5,939,709 | A | * | 8/1999 | Ghislain et al. | ............... | 250/216 |
| 6,489,611 | B1 | * | 12/2002 | Aumond et al. | .................. | 850/3 |
| 7,047,796 | B2 | * | 5/2006 | Lewis et al. | ..................... | 73/105 |
| 2003/0060987 | A1 | * | 3/2003 | Dao et al. | ........................ | 702/42 |

* cited by examiner

*Primary Examiner* — Hezron E Williams
*Assistant Examiner* — Rodney T Frank (57) ABSTRACT

Modifications to the indenter probe tips and transducer, and proper selection of optics in an indentation system allow straight down or slightly angled optical viewing of the sample surface under the indentation tip by a microscope, by providing an optical path through the transducer from the sample surface under the tip to a microscope objective, thereby simplifying alignment of the tip to features on the sample.

4 Claims, 8 Drawing Sheets

OFF-AXIS IMAGING FOR INDENTATION INSTRUMENTS

CROSS-REFERENCE TO RELATED APPLICATIONS

This application is a continuation-in-part of application Ser. No. 11/708,302 filed on Feb. 20, 2007 by the present inventor, now U.S. Pat. No. 7,647,822.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

This invention relates to an optical imaging method for use with indentation instruments.

Indentation instruments use a mechanical probe tip which is typically spherical, conical, or pyramidal in shape, to determine certain mechanical properties of a sample. In traditional indentation, the probe tip is typically forced into the sample using a known force, and the size of the resulting indentation is used to determine the hardness of the sample. In more advanced indentation instruments, the indentation depth is recorded along with the load force. This is done by attaching the tip to a transducer capable of measuring and/or generating force and displacement This is commonly referred to as "instrumented indentation". This technique allows determination of the elastic modulus as well as the hardness. When operating these instruments it is often highly desired if not necessary to align the probe tip to the sample with a high level of precision. This is commonly done using an optical microscope, but since the probe tip, as well as the load and/or depth sensing apparatus for the indentation application blocks the optical path of the microscope, inconvenient means must be resorted to in order to perform the alignment.

For large indentation instruments this is typically accomplished by using a mechanical stage to move the sample back and forth between an optical microscope and the indentation apparatus. Large stages with the required precision to locate a feature on the sample using the microscope and then translate that feature to align with the probe tip with a position error on the order of a micron adds considerable expense to the system, and the added size tends to degrade mechanical stability. In smaller systems the microscope may be tilted so as to avoid the blocking effects by viewing the tip and sample from the side. This avoids the need for the large stage as the sample does not need to be moved between the microscope and probe tip, but viewing the features on the sample that the probe tip is being aligned to is more difficult, since the tilted microscope only has a narrow band of the sample in focus at once.

It would be highly desirable to be able to view the sample surface from directly above, and align a feature on the sample to the probe tip without having to translate the sample back and forth between the optical microscope and the tip, but with current equipment this is not possible. Most currently available transducers and tips are too large to fit between the sample and a microscope objective, and even if they could, the transducers are constructed such that there is no way for light to pass through them. Indenter probe tips are also too large, both in length and diameter, so that they do not physically fit in the available space due to the height, and the excessive diameter blocks the light path of any available microscope objective.

BRIEF SUMMARY OF THE INVENTION

By modifying the probe tip and transducer, and selecting the proper microscope optics it is possible to observe the surface of a sample material directly under a probe tip, thereby allowing the probe tip to be directly aligned to a feature on the sample without moving the sample between the tip and a remotely positioned microscope, or requiring the microscope to be tilted at an angle to view the sample and tip from side, which results in only a very narrow sliver of the sample being in focus. In a first embodiment of the current invention, the transducer is modified by providing an opening through which light may pass near the central region of the transducer, and preferably centered about the probe tip. This opening may be a physical opening, with actual regions cut away from the parts of the transducer, or the transducer may be constructed of transparent materials that allow light to pass through, such as glass to replace opaque or translucent substrate materials such as ceramic or glass-epoxy printed circuit board material, and indium tin oxide to replace opaque metals for electrodes where electrical conductivity is required.

The probe tip must also be modified to provide for a light path to the microscope. The smallest indenter probe tips currently available commercially are 2.0 mm in diameter and 5.5 mm long. They are designed to attach to a transducer by means of a 000-120 stud (which has a diameter of 0.86 mm) in the transducer and the tip has a matching female thread in its base. The probe tips used in this invention are about 0.25 mm diameter and 1.5 mm long. The smaller size of the tip does not hinder or limit the indentation measurements in any way, as the greater size of the commercial tip is used only for mounting the tip to the transducer. Probe tips used for indentation typically consist of a diamond embedded in a metal shank. The diamond has facets ground at angles which vary with the application.

If the angle between the facets and the central axis of the tip is fairly small, such as 30° to 45°, it is possible to select a microscope lens with a wide enough cone of light to in effect see around the probe tip and form an image of the sample directly under the tip. Indentation testing traditionally uses blunter tips, such as the Berkovich, which has an angle of 65.35°. Tips with wide angles such as that are sometimes preferred due to their greater durability. It is generally not feasible to obtain a lens with a cone of light that wide, but it is still possible to image the sample directly under such a tip by grinding the majority of the tip to a cone with a half angle of 30° or less, and grinding the 65.35° indenter facets into only the very end of the tip, so that the indenter portion has a diameter of 0.025 mm or less. Then, by lifting up the tip from the sample surface by a small distance (approximately equal to the diameter of the indenter facets), the blunt portion of the tip is removed far enough to provide a light path for the microscope. The mechanism required to lift the tip that small amount is typically already incorporated into the indentation system. In a second embodiment of the invention, the microscope optics may be positioned slightly to the side, and at a small angle, so as to still point at the probe tip. This second embodiment is especially useful when a larger field of view is desired, as lower power larger field of view objectives are not generally available with the large NA values required to operate coaxially as in the first embodiment described above.

DETAILED DESCRIPTION OF THE INVENTION

In reading the following description and claims, it should be understood that any reference to relative terms such as upper and lower, top and bottom, left and right, are used with respect to the orientation of the object in the referenced drawings, and that simply re-orienting the object does not effect the operating principles of the object or its relation to the scope of the appended claims. The following description uses a particular capacitive transducer as an example, as that transducer is particularly suitable and easily modified for use in the current invention. The description of that transducer given here is simplified so as to provide only those details relevant to the current invention. Specific details of that transducer may be obtained by referring to U.S. Pat. No. 7,046,497 titled "Multi-layer Capacitive Transducer", which is hereby incorporated by reference. Although that patent shows a transducer with terminals for electrical connection to electronic circuitry directly above the transducer, those skilled in the art will immediately understand that the terminals may be easily modified to exit the sides rather than the top, so that the electronic circuitry can be positioned to the side of the transducer where it will not interfere with the optical path.

In order to make the figures more easily understandable, the reference numerals for items of similar function use the same numeral, with an alphabetic suffix pertaining to the location (T for top, C for center, B for bottom). Also, when reference numerals in a subsequent figure refer to items that are similar to, but slightly modified from a previous figure, the reference numerals are incremented by 100.

Figure 1A:
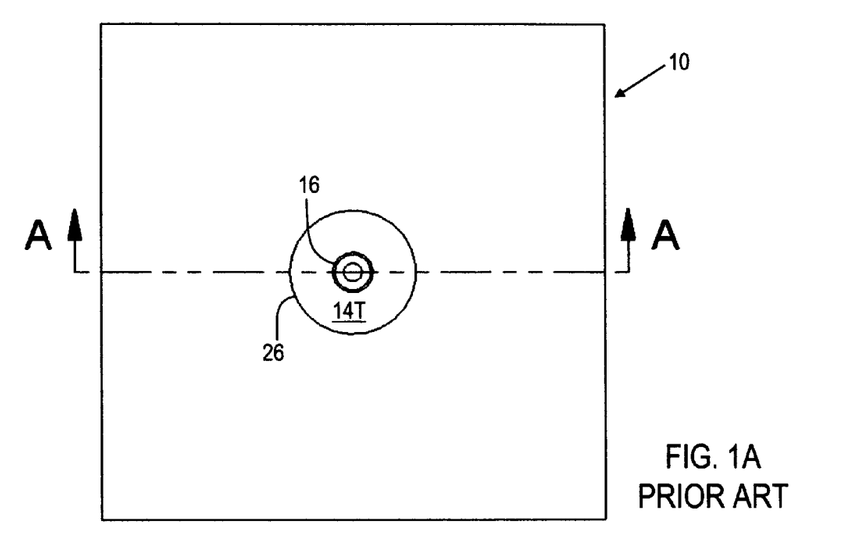
FIG. 1A is a top view of a prior art transducer used for nanoindentation.
Figure 1B:
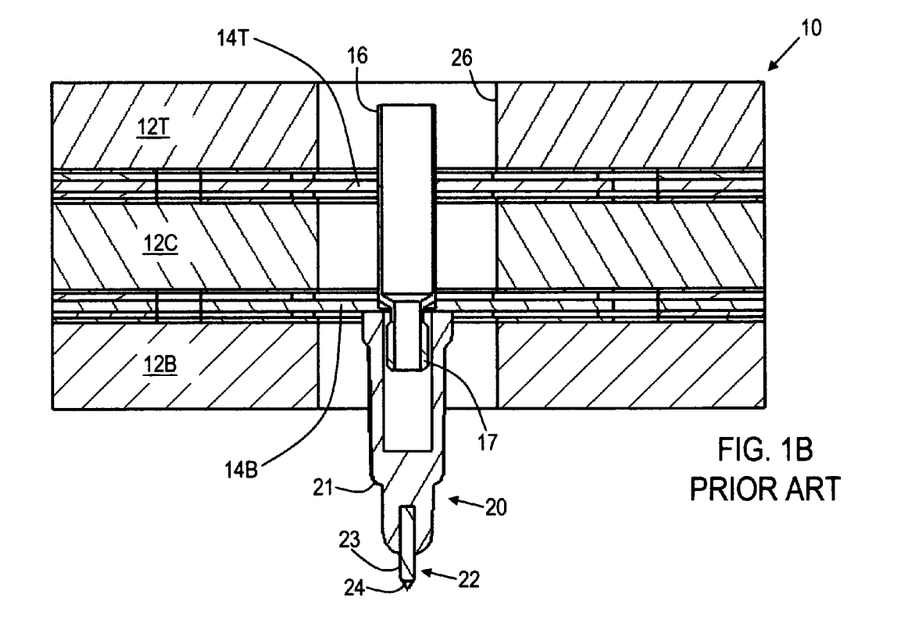
FIG. 1B is a cross sectional view of the transducer as viewed straight from the side.
Figure 1C:
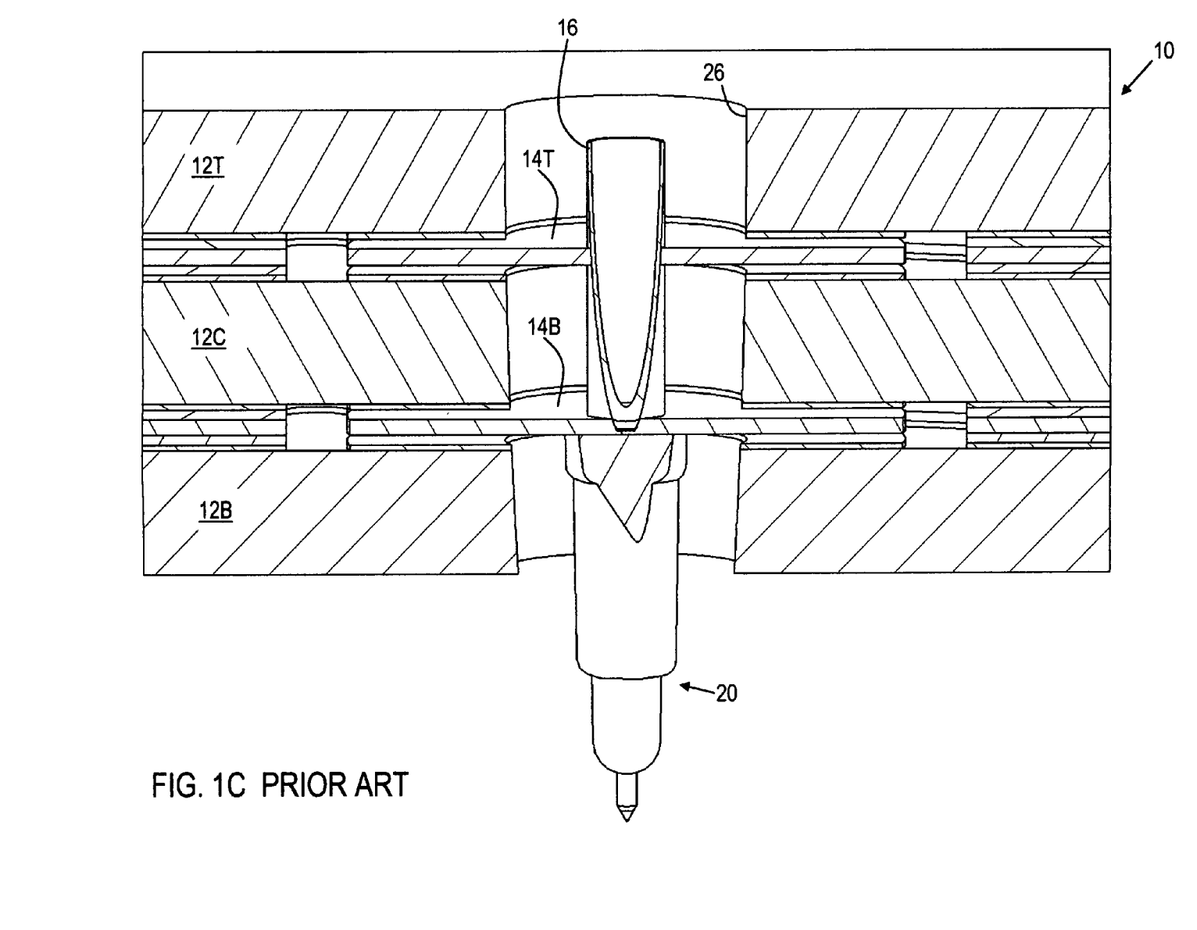
FIG. 1C is a cross sectional view, as seen from an angle slightly higher than in FIG. 1B.

Prior art capacitive transducer 10, suitable for nanoindentation is shown in FIGS. 1A-C. Transducer 10 is small enough to fit between the sample surface and some microscope objective lenses. Although the transducer has a central hole 26 through all three substrates 12T, 12C, and 12B, the optical path is completely blocked by electrodes 14T and 14B. Stem 16 is connected to top electrode 14T and bottom electrode 14B. Stem 16 includes a threaded portion 17 that protrudes below bottom electrode 14B, with a 000-120 male thread. Tip assembly 20 includes holder 21, and tip-shank assembly 22. Holder 21 has a 000-120 female thread on the inner surface to mate with threaded portion 17 of stem 16 for attaching tip assembly 20 to transducer 10. Tip-shank assembly 22 includes metal shank 23 and diamond tip 24. Metal shank 23 has a typical length of 1.5 mm and a diameter of 0.025 to 0.050 mm. It may be glued or press fitted into holder 21.

To understand the current invention it is important to understand a parameter called the numerical aperture (NA) of a lens. The NA of the lens is related to the angle of the cone of accepted light by $NA=\sin(\mu)$, where $\mu$ is half of the total angle of the accepted light cone. The resolution of a lens improves as the NA (and the angle of the cone of light) increase, so higher quality lenses generally have higher NA. Table 1 shows the relationship between NA and $\mu$. Also shown are resolution, depth of focus and working distance for several lenses selected from an Edmund Optics catalog, as well as the price of each.

TABLE 1

Microscope objective optical parameters.

| NA | µ (rad) | µ (deg) | resolution (µm) | depth of focus (µm) | working distance (mm) | Price, USD on Nov. 15, 2009 | Lens # | Description |
|---|---|---|---|---|---|---|---|---|
| 0.25 | 0.25 | 14.5 | — | — | 1.5 | 93 | 1 | Commercial Grade 10X Plan U43-907 |
| 0.45 | 0.47 | 26.7 | 0.74 | 2.7 | 19 | 1500 | 2 | EO 10X NT58-372 |
| 0.55 | 0.58 | 33.4 | 0.5 | 0.9 | 13 | 2340 | 3 | Mitutoyo 50X M Plan Apo NT46-146 |
| 0.60 | 0.64 | 36.9 | 0.56 | 1.5 | 13 | 1750 | 4 | EO 20X NT58-373 |
| 0.70 | 0.78 | 44.4 | 0.4 | 0.6 | 6 | 3030 | 5 | Mitutoyo 100X M Plan Apo NT46-147 |
| 0.75 | 0.85 | 48.6 | 0.3 | 0.5 | 5.2 | 4970 | 6 | Mitutoyo 50X M Plan Apo HR NT58-237 |
| 0.90 | 1.12 | 64.2 | 0.3 | 0.3 | 1.3 | 5350 | 7 | Mitutoyo 100X M Plan Apo HR NT58-238 |
| 0.14 | 0.14 | 8.0 | 2 | 14 | 34 | 525 | 8 | EO 5X NT59-876 |
| 0.28 | 0.28 | 16.3 | 1 | 3.58 | 33.5 | 650 | 9 | EO 10X NT59-877 |
| 0.42 | 0.43 | 24.8 | 0.7 | 1.6 | 20 | 1625 | 10 | EO 20X NT59-878 |

Table 1 shows that a lens such as number 4 with an NA of 0.6 has a μ of 36.9°. Such a lens placed directly above an indenter tip with an angle from the face to the central axis of 30° (such as a 60° cone) would allow a small amount of light from the region of the sample at the point of the tip to be collected by the lens and form an image of the sample under the tip. Selecting lens number 6, with an NA of 0.75 and μ=48.6° would allow substantially more light from the sample to be collected by the lens, forming a brighter and more satisfactory image.

Figure 2A:
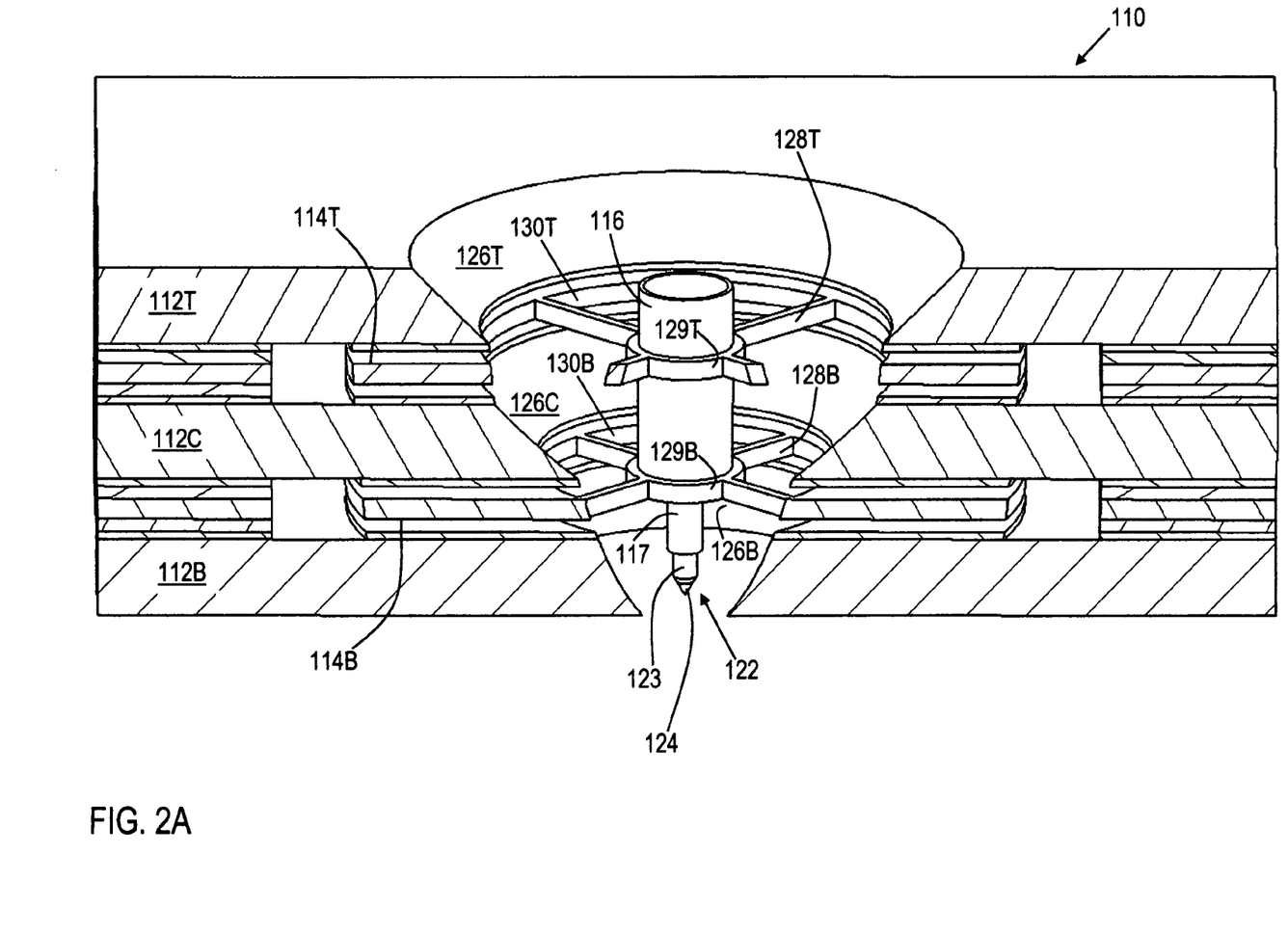
FIG. 2A is a cross sectional view of a transducer modified to provide a light path through the transducer. The viewing angle is similar to that in FIG. 1C.

It is also necessary to modify the transducer to provide a path for the light from the sample to the lens. FIG. 2A shows transducer 110, which has been constructed to allow unobstructed passage of light through it, between the sample surface under the indenter tip and a lens of NA 0.6. Substrate 112B may be identical to substrate 12B of transducer 10, but substrates 112C and 112T are modified by tapering and widening central holes 126C and 126T, to correspond with the 36.9° half angle of the cone of accepted light entering the NA 0.6 lens. Electrodes 114B and 114T are modified by providing openings 130B, 130T for the light to pass through. Beams 128B and 128T connect electrodes 114B, 114T to stem 116 by collars 129B, 129T. The upper portion of stem 116 may be identical to stem 16 of transducer 10, but the lower threaded portion has a reduced diameter, and is threaded on the inside, rather the outside, so that shank 123, which has male threads (not shown) on its upper portion, may be threaded directly into lower stem portion 117 without requiring the much larger holder 21 used with transducer 10. Shank-tip assembly 122 also includes diamond tip 124. The main reason for the large size of holder 21 was to provide an open space under the transducer for viewing with a microscope tilted at an angle. This is of course rendered unnecessary by the current invention.

Figure 2B:
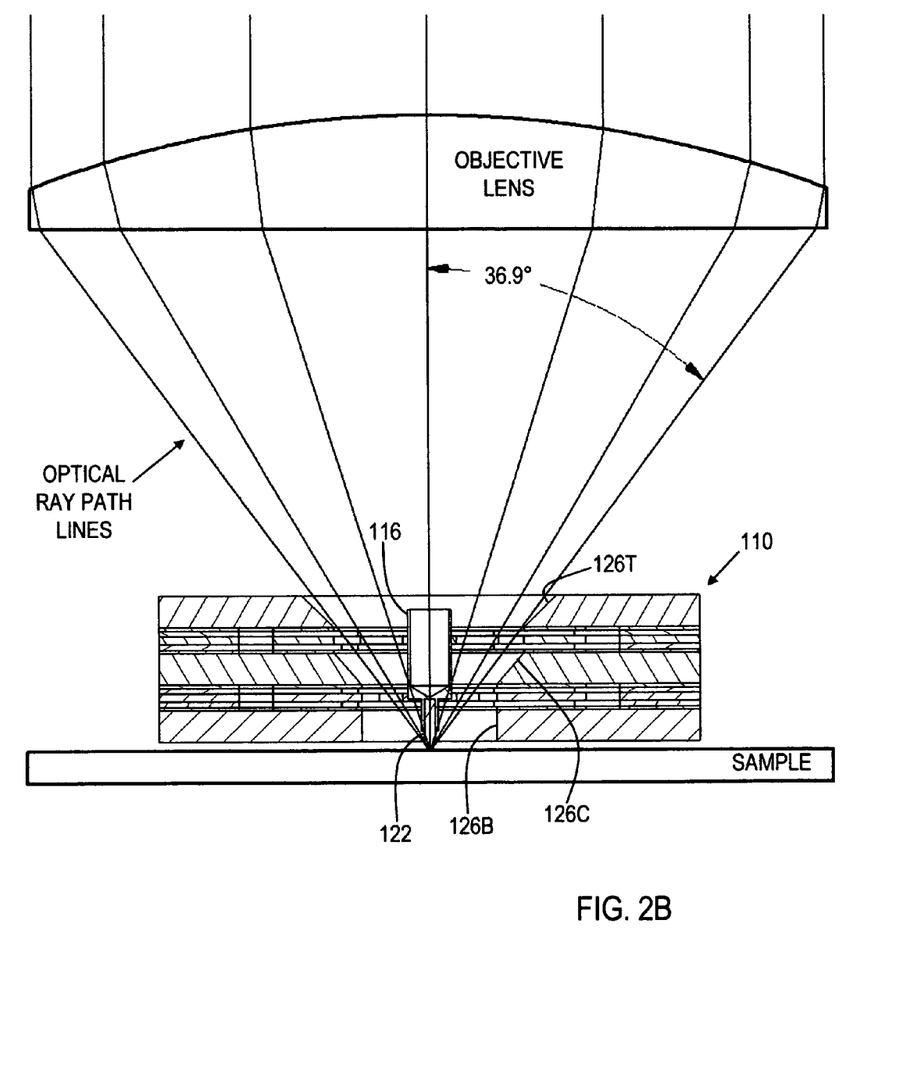
FIG. 2B is a cross sectional view of the modified transducer, as viewed straight from the side, and also including a diagrammatic view of a sample, a lens, and the path taken by optical rays through the lens and transducer to the sample surface.

FIG. 2B shows a straight side view cross section of transducer 110, with a diagrammatic view of a sample and lens 4 (NA=0.6) from Table 1. By eliminating the unnecessary length from the indenter tip, openings 130T, 130B in electrodes 114T, 114B sized to allow passage of the 36.9° half angle light cone from a lens with NA=0.6 still leaves approximately 75% of the area of bottom electrode 114B and 50% of the area of top electrode 114T. For some applications, top electrode 114T is not required to provide an electrical function, but only serves as a mechanical support for stem 116, to increase the resistance to angular deflection caused by side loads at diamond tip 124. In this case, the diameter of opening 130T may be increased so that electrode 114T is reduced to a narrow ring similar to collar 129T. With a corresponding increase in the size of central holes 126T and 126C, the transducer can be made to pass the light cone from a lens of NA 0.75, such as lens 7 from Table 1, for a brighter, more satisfactory image of the sample. Since lens 7 has a working distance of 5.2 mm, which very close to the thickness of transducer 110, it is also desirable to reduce slightly the thickness of substrates 112T, 112C and 112B to ensure adequate clearance. If the electrical function of top electrode 114T is required, it is a simple matter to increase its diameter.

Figure 3A:
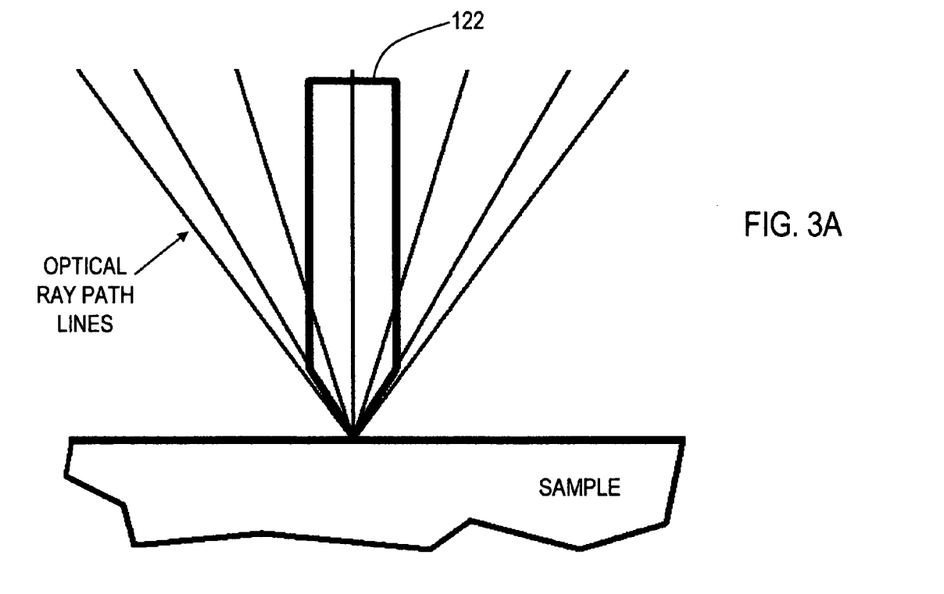
FIG. 3A is a diagrammatic view of the relationship between the optical path rays of a lens of NA 0.6 and an indenter probe tip with a total included angle of 70°.
Figure 3B:
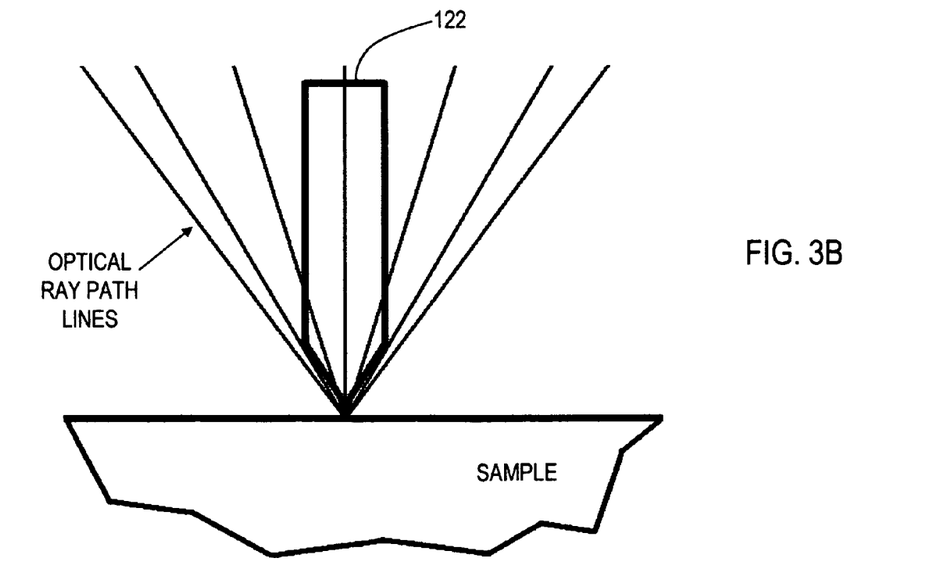
FIG. 3B shows that slightly raising the indenter probe tip increases the number of optical rays that clear the tip and reach the sample surface, thereby improving the imaging ability.

FIG. 3A shows a diagrammatic view of tip-shank assembly 122, which has a point with a 70° total included angle, a sample surface and the light path for lens 4 from Table 1 (NA 0.6). It can be seen from that figure that only the outermost optical rays clear the tip and are able to reach the lens to form an image of the sample surface under the tip. FIG. 3B shows the same items as FIG. 3A, but in FIG. 3B the tip 122 has been elevated from the sample surface by 0.025 mm. This has substantially increased the unobstructed optical path, so that the image quality will be substantially improved. Transducers such as transducer 110 have the ability to actuate in such a manner without any added mechanism, so the image quality may be improved by simply pulling the tip slightly away from the sample during the optical imaging and tip alignment operation prior to performing the indentation. Substituting a larger NA lens such as lens 6 with NA 0.75 will also substantially increase the image quality.

Figure 4:
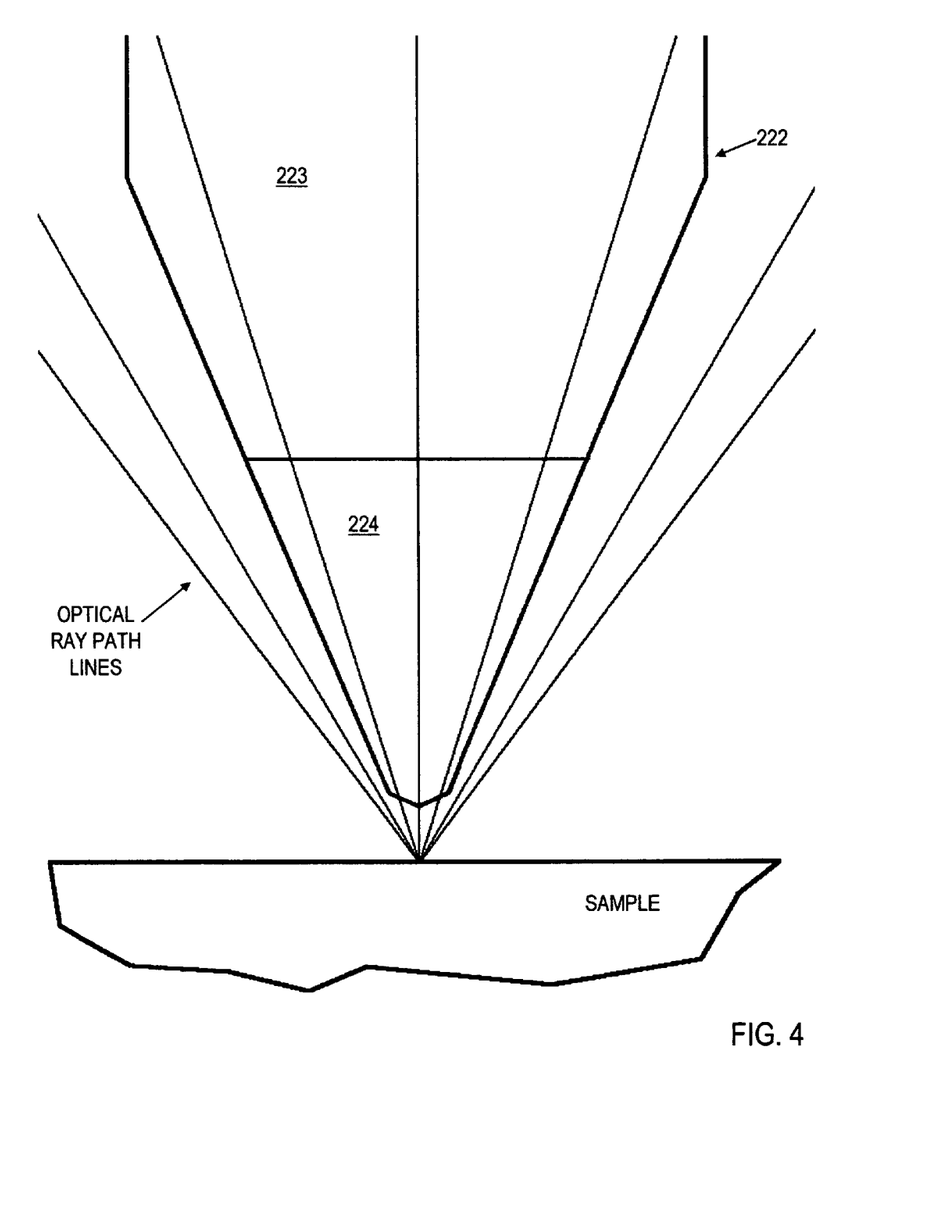
FIG. 4 is a diagrammatic view of the relationship between the optical path rays of a lens of NA 0.6 and an indenter probe tip raised 0.025 mm above a sample surface, where the majority of the probe tip has a total included angle of 45°, but the region closest to the sample has an angle of 130.7° and a width of 0.025 mm. Even more of the optical path rays clear the probe tip than in FIG. 3B, thereby further improving the imaging ability.

As previously stated, indentation tips with narrow angles such as 70° or less (35° face to centerline), although desirable for improving the imaging ability of the sample surface under the tip, are sometimes not desirable due to their fragility when indenting hard samples such as tool steel, ceramics or carbides. For these materials, tips such as the Berkovich, with a face to center line angle of 65.35° are often used. Reference to Table 1 shows that even lens 7, with NA 0.9 does not have a wide enough light cone to image the sample surface under that tip, when the tip is in contact with the sample. These impediments may be traversed by fabricating a specially shaped tip as shown in FIG. 4, and raising the tip above the sample surface slightly as shown in FIG. 3B while imaging. Tip-shank assembly 222 is similar to assembly 122, but the angle of the main portion of diamond 224 and the portion of shank 223 proximate diamond 224 are fabricated with a smaller included angle, such as 45° or less, rather than 60° or 70° as in assembly 122. Due to the small size of nanoindentation indents, a tip having the desired facets of 65.35° fabricated to a width of 0.025 mm as shown in FIG. 4 will cover virtually all applications in nanoindentation. In fact, 99% of the applications will be covered by a tip of only 0.005 mm width. Using tip-shank assembly 222 as just described, and raising the tip from the sample by at least the width of the faceted portion provides the ability to obtain a high quality image of the sample surface directly under the tip, without moving the sample in the lateral directions with a large stage, which would add cost and degrade the mechanical stability of the system.

Figure 5:
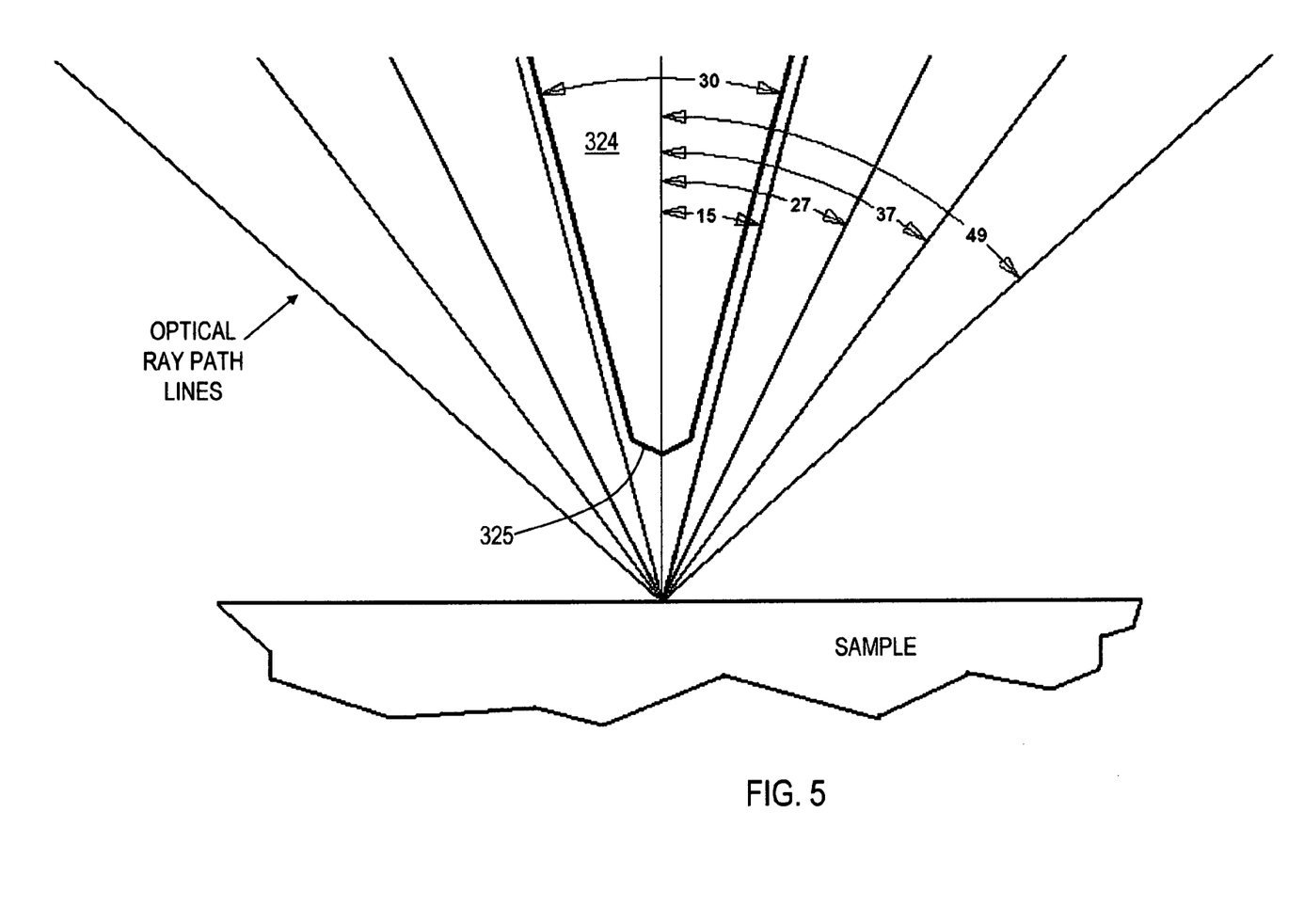
FIG. 5 is a diagrammatic view showing the relationship between the outermost optical path rays for four lenses from Table 1 and an indentation tip modified to improve the optical imaging capability.

FIG. 5 is a diagrammatic view of a portion of a diamond indenter tip 324, and the relationship of the optical paths of four lenses from Table 1 to said tip and a sample. Tip 324 has been modified to provide superior imaging without sacrificing durability. The construction of this tip assembly is the same as assembly 222, except that the angle of the lower portion of the shank (not shown) and diamond tip 324 are smaller, at 30°, and the width of faceted portion 325 of tip 324 is reduced to 0.010 mm. The four optical path rays identified by their angle from the central axis at 15°, 27°, 37° and 49° correspond to the outermost rays of lenses 1, 2, 4 and 6 from Table 1, with corresponding NA of 0.25, 0.45, 0.60 and 0.75. The height of the tip above the sample surface is 0.025 mm. The angles are rounded to the nearest degree. Lens 1 has an actual half angle of 14.5°, so its outermost ray will run into the tip at some point beyond that shown in the figure, and no light from the sample directly under the tip will reach the lens to form an image. For all of the other three lenses a substantial amount of light from the sample will reach the lens. In the case of lens 2, it may appear from a visual comparison between the 15° half angle of the tip and the 27° half angle of the lens that slightly less than half of the total possible light (as would reach the lens without the obstruction from the tip) will reach the lens, but one must consider the relative areas of the circular portions of the projections of the cones, not the linear lengths from the cross section shown in FIG. 5. Taking the actual areas into account, the ratio of actual light passed to the maximum possible for an unobstructed lens is 72% for lens 2 (NA 0.45), 87% for lens 4 (NA 0.60), and 94% for lens 6 (NA 0.75). It is therefore possible to obtain an image of the sample surface directly under the tip, with a quality nearly as good as if the tip were not present.

An alternative to providing openings 130T, 130B in electrodes 114T, 114B is to modify the structure of the electrodes, Rather than fabricating the electrodes out of metal, as is normally done, the electrodes may be fabricated by depositing a transparent, electrically conductive coating such as indium tin oxide on a transparent support structure such as glass. Substrates 112T, 112C and 112 B are also fabricated out of glass or some other transparent material.

Figure 6:
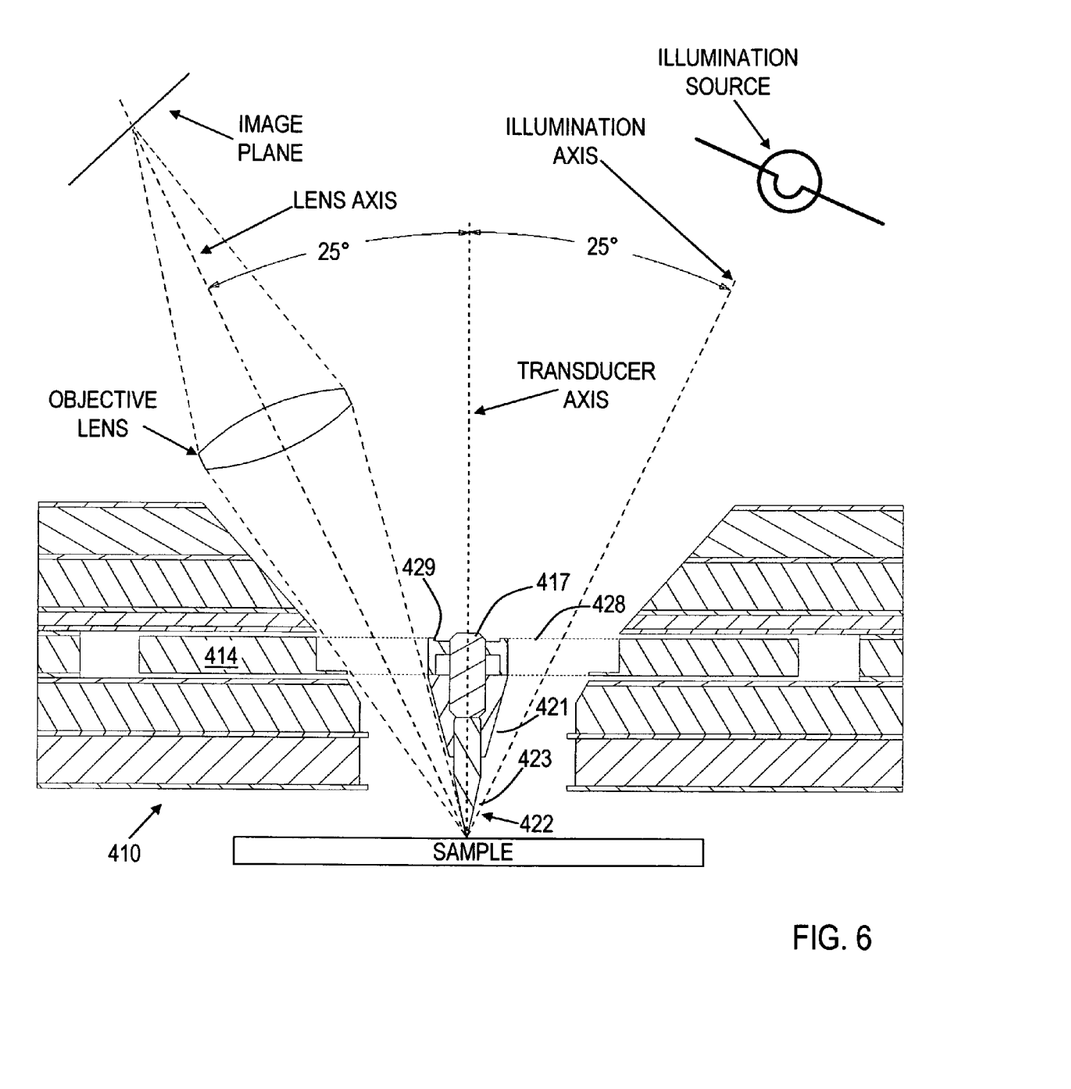
FIG. 6 is a diagrammatic view showing the optical path for an off axis system, where the axis of the microscope is at an angle from the axis of the transducer.

FIG. 6 is a diagrammatic view of a second embodiment of the current invention, wherein the microscope is positioned at a small angle from the axis of the transducer. This is especially suited for lower power objectives, such as lens #8 or 9 in Table 1. These lenses provide a wider field of view than lenses 3-6, and are also much cheaper, but because of their smaller NA, they have lower resolution, and are not well suited for use in the first embodiment, where the objective lens is positioned directly above the probe tip. In FIG. 6 the axis of the objective lens is shown at an angle of 25 degrees from the axis of the probe tip (and transducer). This is presented as a typical useful value only and actual angles me deviate from that value, based on the actual design and dimensions of transducer 410. The important point is that the angle is substantially smaller than in the prior art, where the axis of the objective is tilted at more than 45 degrees, typically 60 degrees or more, in order to view the region of the sample proximate the tip from under, rather than through the transducer. This provides a much less distorted perspective view of the sample.

Transducer 410 is of a somewhat different configuration than the prior ones, having a single moving rotor electrode 414. Collar 429 for attaching probe tip assembly 422 functions in the same manner as previously disclosed versions. Beams 428 (shown at dotted lines since they do not lay in the cross section of the transducer shown in the figure) connect electrode 414 to collar 429 as before, while providing openings for the optical path of the objective lens. Probe tip assembly 422 is configured slightly differently, but is functionally similar. Stud 417 is preferably attached permanently to holder 421, although it could alternately be attached to collar 429. Shank 423 is attached to holder 421 as before. A diamond tip (not shown) may be attached to the end of shank 423 proximate the sample, but of course specific materials used in the probe tip are irrelevant to the scope of the current invention.

The image plane in FIG. 6 is shown tilted at an angle from the lens axis. This is an optional but highly desirable feature that may be used to compensate for the angle between the axis of the objective lens and the sample, so that the entire image, rather than only a small sliver, is in focus. Note that FIG. 6 is not to any particular scale, in particular, in an actual system the distance from the objective lens to the image plane is typically several times greater than the distance between the lens and the sample.

Illumination for the microscope may be provided in various forms, depending on the reflective and transmissive properties of the sample. For transparent samples, illumination could be provided from the bottom of the sample, but the majority of typical samples are not transparent, so illumination must be provided from the front. Non-specular surfaces may have the illumination applied from the front at various angles, but specular (mirror like) samples, which are common in this application, require illumination that is normal to the sample, or the majority of the illumination will be lost. For systems where the optics are normal to the sample surface, as in the first embodiment, this may be done using commercially available adaptors which use prisms or partially reflective mirrors to accept a beam of light normal to the axis of the microscope and divert it to become coaxial. The light then exits the objective, reflects of the sample and directly back into the objective.

For the second embodiment of this invention, this standard coaxial, or in line illumination is not preferred, since when used on a specular sample, the illumination leaving the objective will not reflect off the sample back into the objective, but will follow a path to the right of the transducer axis that mirrors the axis of the objective lens on the left side of the transducer axis. The solution to this problem is to apply the illumination on an axis to the right hand side of the transducer axis that mirrors the axis of the objective lens, so that the illumination that reflects off the sample follows the axis of the objective into that lens.

Several specific embodiments have been described, giving specific details including dimensions, design details, process information, and suggested materials. These specific details in no way limit the scope of the invention. Likewise, those skilled in the art will realize many small changes in the shape, size, and position of components that can be made without exceeding the scope of this invention. Although capacitive transducers were used as examples, any load-displacement transducer or combination of transducers capable of measuring or generating load and/or displacement, such as strain gauge, electromagnetic voice coil, piezoelectric, laser/photodiode or any other may be used to perform the nanoindentation or other material property or topography measurement, where the measurement is based on the interaction of a mechanical probe with the sample, without departing from the scope of the invention as defined by the following claims:

I claim:

1. In a mechanical probe based measurement instrument including a sample, a transducer having a central axis, a tip attached to the transducer, and an optical system including at least one lens with a central axis, wherein the axis of said lens is rotated away from the axis of said transducer, the improvement comprising an unobstructed optical path between the sample and the lens, whereby the lens forms an image of the sample surface proximate the tip, allowing the tip to be aligned to a particular portion or feature on the sample without the use of a lateral travel stage, and without requiring a lens of 0.6 numerical aperture or larger;

wherein the transducer is located between the lens and the sample, and the unobstructed optical path is provided by at least one hole in the structure of the transducer, the at least one hole being located proximate said tip.

2. The instrument of claim 1, further including image sensing means including an image plane, wherein the image plane is tilted at a non-perpendicular angle with respect to the axis of said lens, thereby compensating for the non-perpendicularity between the axis of said lens and the sample, in order to provide a focused image over the entire image plane.

3. The instrument of claim 1, further including an illumination system wherein the illumination is applied to said sample along an axis that has mirror symmetry with the axis of said lens, the axis of said transducer being in the plane of symmetry.

4. In a mechanical probe based measurement instrument including a sample, a transducer having a central axis, a tip attached to the transducer, and an optical system including at least one lens with a central axis, wherein the axis of said lens is rotated away from the axis of said transducer, the improvement comprising an unobstructed optical path between the sample and the lens, whereby the lens forms an image of the sample surface proximate the tip, allowing the tip to be aligned to a particular portion or feature on the sample without the use of a lateral travel stage, and without requiring a lens of 0.6 numerical aperture or larger;

wherein the transducer is located between the lens and the sample, and the unobstructed optical path is provided by fabricating said transducer at least partially from optically transparent material.

\* \* \* \* \*